United States Patent [19]
Ehlers

[11] Patent Number: 5,224,497
[45] Date of Patent: Jul. 6, 1993

[54] METHOD OF REMOVING DIVERTICULA IN THE COLON

[76] Inventor: Robert L. Ehlers, 414 Rehnberg Pl., West St. Paul, Minn. 55118

[21] Appl. No.: 820,552

[22] Filed: Jan. 14, 1992

Related U.S. Application Data

[60] Division of Ser. No. 611,439, Nov. 13, 1990, Pat. No. 5,100,419, which is a continuation of Ser. No. 512,546, Apr. 17, 1990, abandoned, which is a continuation of Ser. No. 215,868, Jul. 6, 1988, abandoned.

[51] Int. Cl.$^5$ .............................................. A61B 17/12
[52] U.S. Cl. ..................................... 128/898; 606/140
[58] Field of Search ............... 606/140, 141, 139, 149, 606/115, 114, 110, 111, 112, 113; 128/898

[56] References Cited

U.S. PATENT DOCUMENTS

| | | |
|---|---|---|
| 3,545,444 | 12/1970 | Green et al. . |
| 3,643,653 | 2/1972 | Takahashi et al. . |
| 3,870,048 | 3/1975 | Yoon . |
| 3,911,923 | 10/1975 | Yoon . |
| 3,967,625 | 7/1976 | Yoon . |
| 3,985,138 | 10/1976 | Jarvik . |
| 3,989,049 | 11/1976 | Yoon . |
| 4,038,988 | 8/1977 | Perisse . |
| 4,085,743 | 4/1978 | Yoon . |
| 4,103,680 | 8/1978 | Yoon . |
| 4,257,419 | 3/1981 | Goltner et al. . |
| 4,257,420 | 3/1981 | Terayama . |
| 4,374,517 | 2/1983 | Hagiwara . |
| 4,374,523 | 2/1983 | Yoon . |
| 4,493,319 | 1/1985 | Polk et al. . |
| 4,735,194 | 4/1988 | Stiegmann . |

OTHER PUBLICATIONS

"Endoscopic Esophageal Varix Ligation: Preliminary Clinical Experience" by Greg van Stiegmann, M.D. and John S. Goff, M.D., from *Gastrointestinal Endoscopy*, vol. 34, No. 2, 1988, pp. 113-117.

"A New Endoscopic Elastic Band Ligating Device" by Greg van Stiegmann, M.D. et al., from *Gastrointestinal Endosocopy*, vol. 32, No. 3, 1986, pp. 230-233.

*Primary Examiner*—Michael H. Thaler
*Attorney, Agent, or Firm*—Merchant, Gould, Smith, Edell, Welter & Schmidt

[57] ABSTRACT

The present invention is a medical device for inverting diverticulum and closing such diverticulum in the inverted position. The apparatus includes a reciprocating vacuum tube for inverting the diverticulum and a caliper for placing a fastening device such as an elastic band around the base of the diverticulum.

10 Claims, 5 Drawing Sheets

METHOD OF REMOVING DIVERTICULA IN THE COLON

This is a division of application Ser. No. 07/611,439, filed Nov. 13, 1990, which is a continuation of Ser. No. 07/512,546, filed Apr. 17, 1990, now abandoned, which is a continuation of Ser. No. 07/215,868, filed Jul. 5, 1988, now abandoned.

FIELD OF THE INVENTION

The present invention relates to medical devices and more particularly to a device for observing and removing diverticula from the intestine.

BACKGROUND OF THE INVENTION

About half of the population over age 50 in developed countries has diverticula which are outpouches or pockets in the colon. Such diverticular often become infected resulting in diverticulities.

Diverticulities is a disease in which the small pockets in the intestinal wall accumulate food reside materials which ferment, developing balloon-like pockets filled with gaseous material. The fermentation causes enlargement of the pockets, often resulting in discomfort. Sometimes the pockets rupture causing life-threatening peritonisis.

In the past, diverticulitis has been treated in various ways. The patient may be treated with drugs that minimize the fermentation reaction in the large intestine. This treatment results in some improvement, however, many pockets are closed off and thus the drugs do not readily enter the pockets. The patient may be placed on a diet which excludes food materials which are likely to cause the development of gaseous materials. For example, members of the cabbage and bean products may be eliminated from the diet.

Diagnoses of diverticulitis may be difficult. In some instances the patient is given a barium enema which coats the lining of the large intestine. X-rays are then taken and the diverticula are identified. In those instances where the pockets are closed off due to inflammation, the barium may not readily enter the pockets. In such instances, the large intestine may be injected with pressurized air which tends to enlarge the intestine, opening the pockets and permitting the barium to enter such pockets. The injection of air, of course, is a significant discomfort.

In other instances, diagnoses of diverticulitis is accomplished using a fiberoptic scope. The scope may be of the type illustrated by U.S. Pat. No. 3,643,653. Such devices include a viewing port which is connected to optic fibers running the length of a tube. The tube is inserted into the colon of the large intestine. The tube includes control mechanism that permits movement of the tube to a position adjacent the lining of the large intestine. The viewing device and the fiber optics are used to observe the lining and thereby identify the diverticula.

Upon observation of a significant diverticula problem, removal of a portion of the large intestine may be dictated. Such an operation has in the past required incision through the abdominal wall. A major surgery. Because of the seriousness of the operation, removal of diverticula sections in the past have been limited to only those cases where the diverticulitis is a very acute. Most persons having diverticular condition have in the past been required to suffer discomfort at various period throughout their life.

The present invention provides a device for removal of diverticula without incision. The present invention also provides a method for treating diverticular without incision through the abdominal wall.

Cl SUMMARY OF THE PRESENT INVENTION

The present invention provides a medical device, including an elongated tube, carrying a plurality of optical fibers together with a viewing device that permits observation through the optical fibers. The tube may also include a vacuum tube for vacuumizing the diverticula to invert such diverticula. Mechanism is included for securing the diverticula in the inverted condition, thereby resulting in the adjacent external wall of the diverticula fusing e.g., growing together. This securing mechanism may be a device for placing a rubber band or a plurality of rubber bands around the diverticula. Alternatively, the mechanism may include a stapling device which staples the inverted diverticula or mechanism for securing a noose around the inverted diverticula.

The device of the present invention may be somewhat similar in structure to the Pentax Flexible Fiber Optic Sigmoid Scope, Model 35, or similar devices made by Olympus with certain modifications or improvements. Such devices have been used in the past for observation within the colon. The present invention modifies and improves such previously existing scopes to permit not only observation, but also treatment of the diverticula.

The present invention consists of a flexible tubal extension to the suction oriface of the scope. The tubal extension may include a Teflon-coated or lubricated sleeve on which is mounted either stretched small rubber bands or pre-tied nylon or biodegradable nooses or surgical staples which can be manipulated by controls attached to the scope at a location outside of the body of the patient. During use, the tubal extension is guided to the entrance of the diverticulum in the colon using the fiber optic viewer which is embedded in the flexiscope. Once in place, the scope controls may be operated to create a vacuum in the tubal extension, thereby pulling the diverticula onto an inverted condition. Using the scope controls, the operator may then apply the vacuum to invert the diverticula extending such diverticula into the colon. The operator would then move the sleeve past the end of the tube, over the inverted diverticula to the colon wall. Using a special caliper, the operator may ease the rubber band, pre-tied noose or staple from the sleeve to around the base of the inwardly extending diverticula. If rubber bands are used, the stretched bands would retract, closing the end of the base of the diverticula. Over a period of several days, the tissue edges of the colon wall would grow together. The diverticula tissue would die and drop off to be excreted or removed through the lower end of the colon. If pre-tied nooses are used, the caliper would provided for slipping the noose off the sleeve. The noose would be attached to the caliper such that manipulation would draw the slip knot of the noose to close the diverticula. Again, the tissue would grow together and the diverticula would die and drop off. If surgical staples are used, a spring-loaded stapler would move a staple off the end of sleeve, closing the base of the diverticula.

The method of the present invention includes the steps of identifying enlarged problem diverticula, applying a vacuum to the diverticula in order to invert or turn such diverticula inside out. The method includes the further step of surrounding the base of the diverticula with a closure mechanism such as a rubber band or a staple. The exterior walls of the diverticula then grow together and the inverted diverticula dies and disintegrates.

IN THE DRAWINGS

DETAILED DESCRIPTION OF THE PRESENT INVENTION

Figure 1:
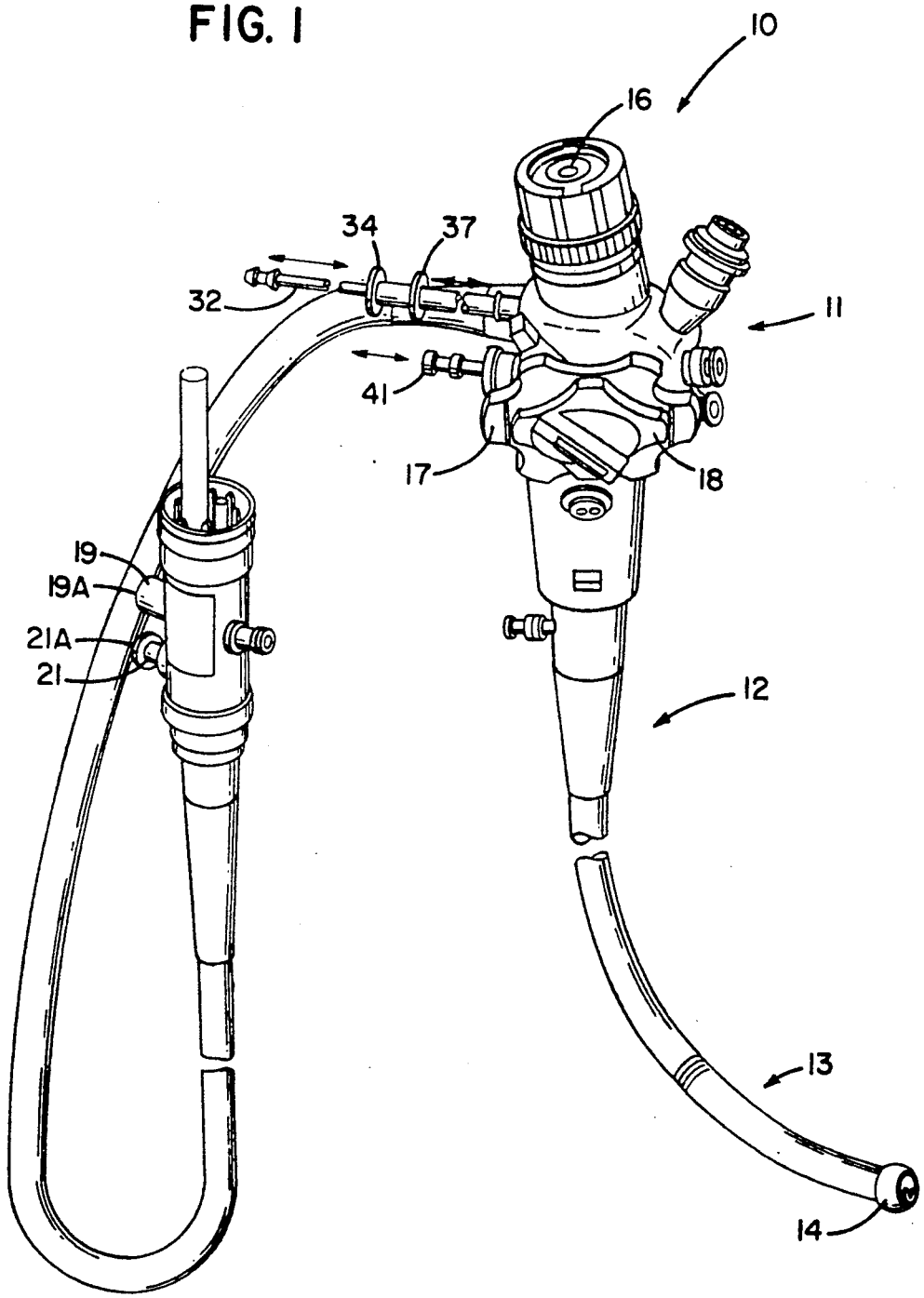
FIG. 1 is a perspective view of the device of the present invention.

The endoscopic apparatus 10 (FIGS. 1-7) of the present invention includes a control housing 11 and an elongated tube 12. The tube 12 has a bendable portion 13 adjacent to the forward end 14. The tube 12 has an image transmitting optical system commencing in the end at portion 14 and terminating in the eye piece 16 of the housing 11. In order to illuminate the object, the optical system may include a plurality of light conducting fibers which are adjacent to a plurality of optical fibers that return an image to the lens 16.

The bendable portion 13 may be controlled in a conventional manner by wires extending through the elongated tube 12. The wires may be controlled by knob 17 for movement upwardly and downwardly and by knob 18 for movement rightwardly and leftwardly. The endoscopic apparatus may include mechanism for injecting water and air through the elongated tube 12. A water channel 19 and an air channel 21 may be extended from inlets 19a and 21a along tube 12 to opening 22.

For example, a water inlet 19 and an air inlet 21 may selectively provide ejection of water and/or air through opening 22. For example for purposes of cleaning an area in the colon for observation and treatment.

The present endoscopic apparatus 10 may include mechanism 26 for inversion and tying off of the diverticula. The mechanism 26 may include a tripod-like support 27 having a ring 28 supported on legs 29, 30 and 31. The base of the legs 29, 30 and 31 may be secured to the distal end 14 of the scope. The diverticulum mechanism 26 further includes a reciprocating vacuum tube 32 which has a tapered outer end 33. Vacuum tube 32 extends along flexible tube 13 into control housing 11 and from thense out to a vacuum source. A rotatable drive 34 may be operated to reciprocate the vacuum tube 32 as will be hereinafter described.

The diverticulum mechanism 26 further includes a fastener applying to controls 37. The control 37 may likewise be a rotatable mechanism for reciprocating the tube 36. Tube 36 may be tapered at its forward end and be adapted to receipt of a plurality of rubber bands such as 38. The size of the rubber bands 38 may be small enough such that they are stretched and applied over tube 36. The bands 38 tightly grip the diverticula when applied to the base of the diverticula.

Figure 7:
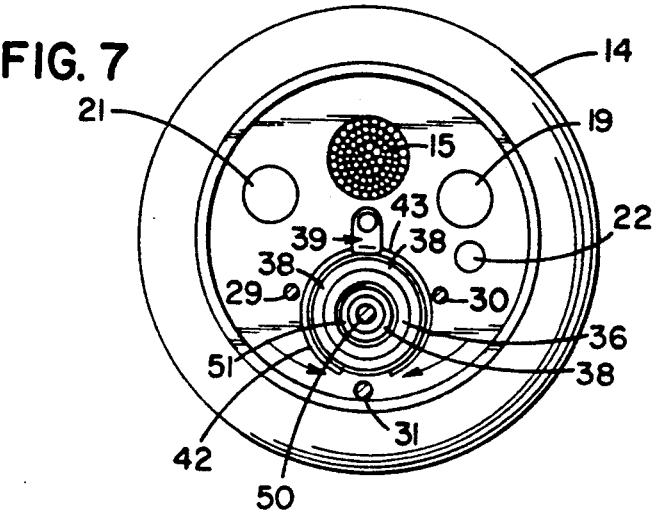

The diverticula mechanism 26 has a caliper 39 which may be reciprocated using controls 41 to maneuver one or more selected rubber bands 38 forwardly off the end of tube 36. The caliper 39, as illustrated in FIG. 7, has a first portion 42 and a second portion 43. The portions 42 and 43 may be biased toward each other and the control 41 may overcome the bias to open the caliper and permit movement along the series of rubber bands.

OPERATION OF THE PRESENT INVENTION

Figure 2:
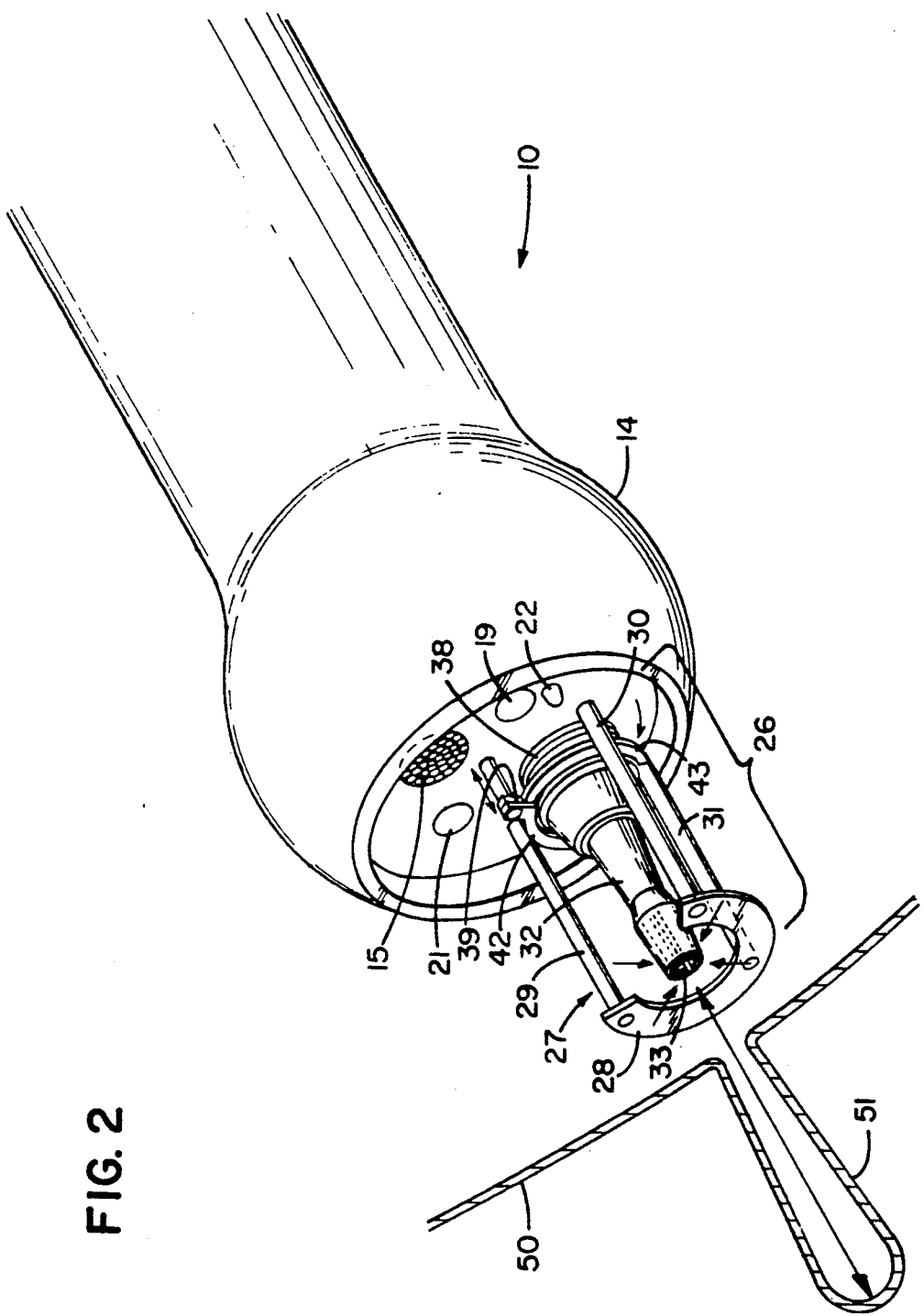
FIG. 2 is a perspective view of the forward end of the present invention.
Figure 3:
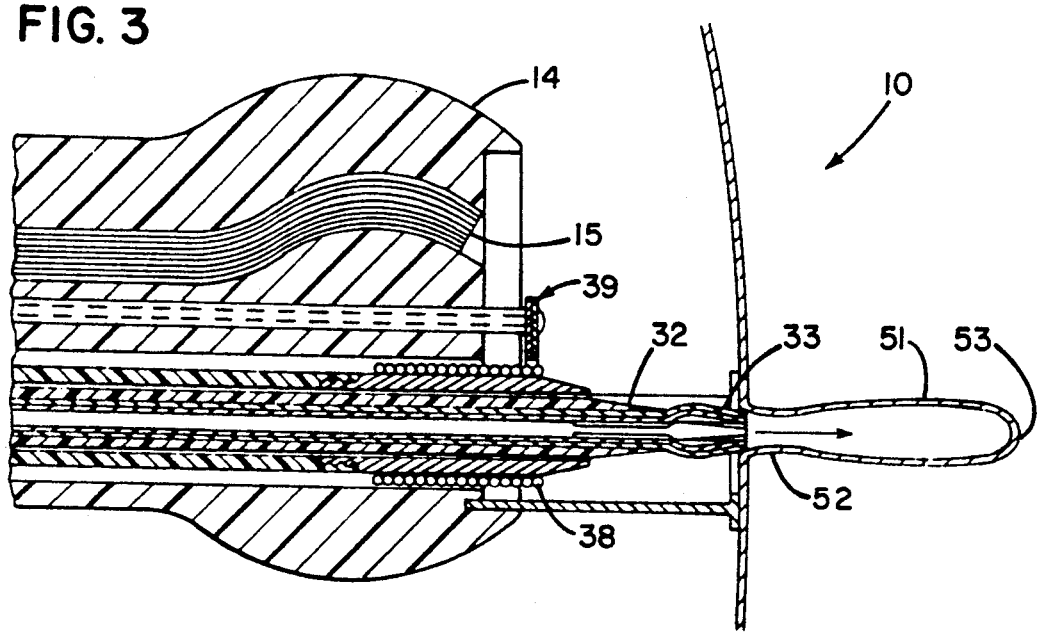
FIGS. 3 through 7 are cross-sectional views of the present invention in various operating positions.
Figure 4:
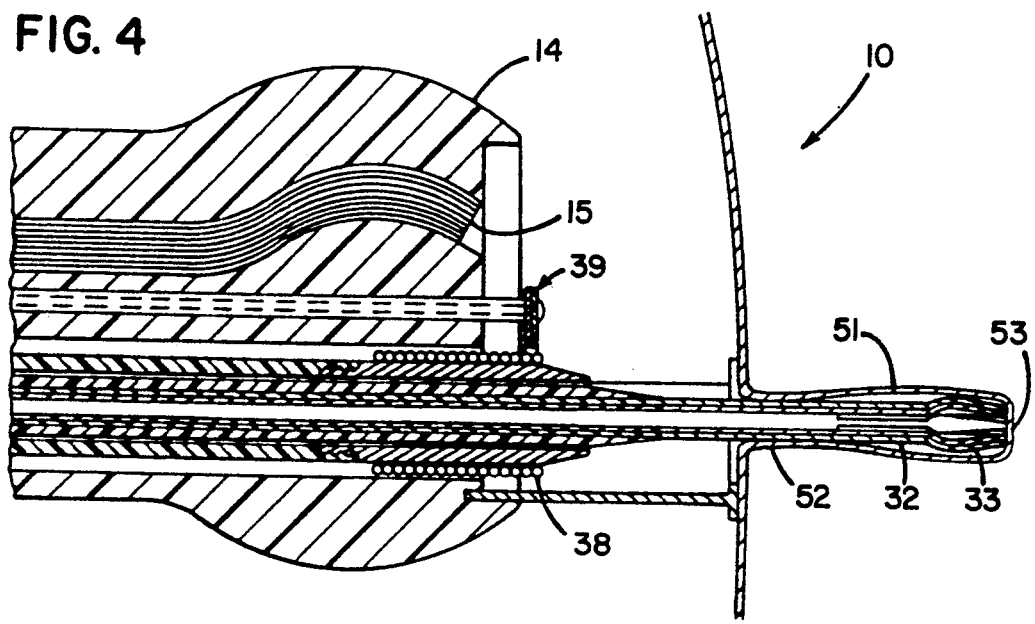
Figure 5:
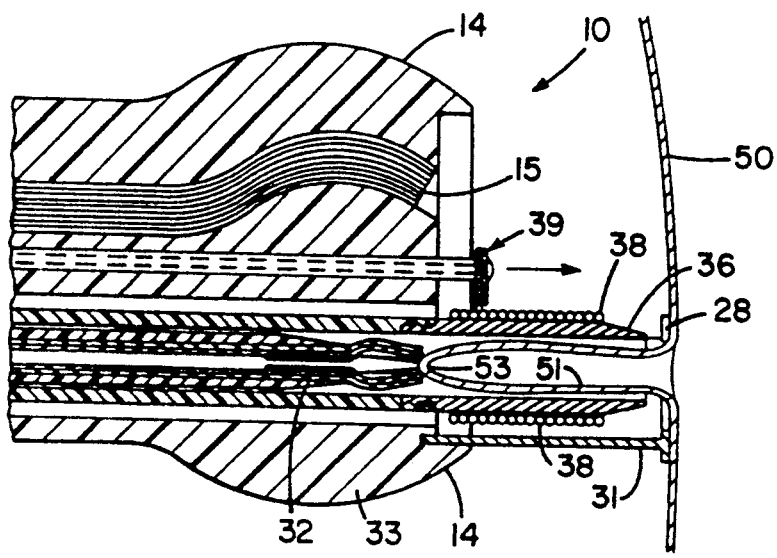
Figure 6:
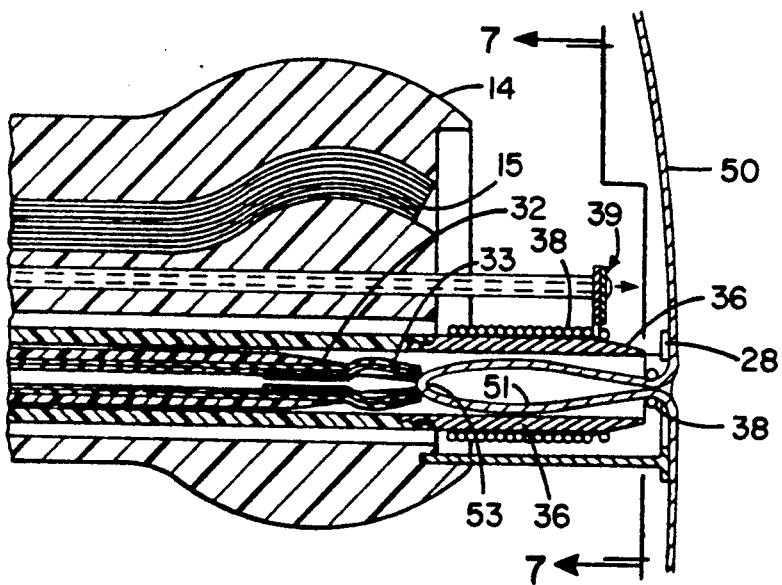
Figure 8:
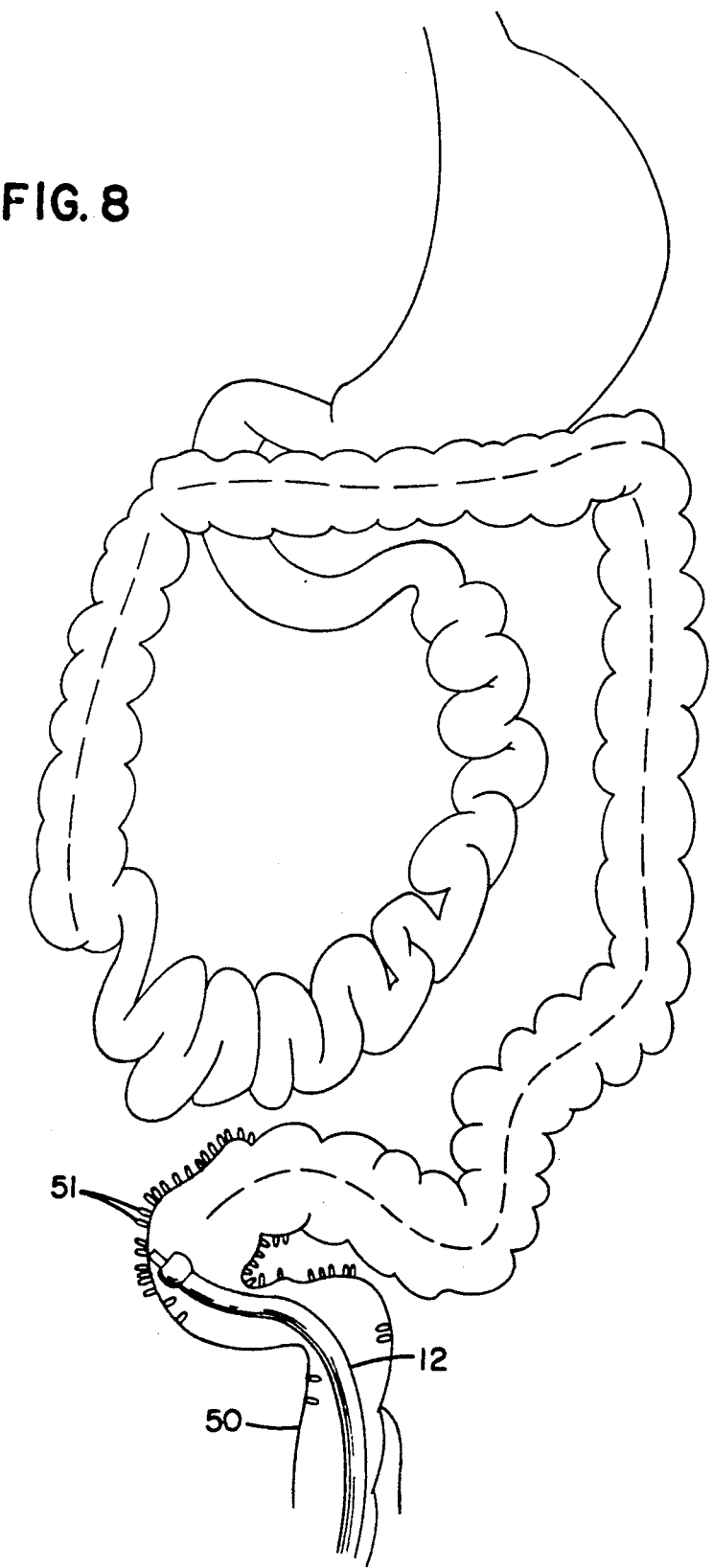
FIG. 8 shows the present invention inserted into the colon.

As illustrated in FIG. 8, the elongated tube 12 of the endoscopic apparatus 10 may be inserted into the patient's colon 50. The control knobs 17 and 18 may be manipulated to bring the forward end 14 of tube 12 to an appropriate diverticula 51. The diverticula 5 is an elongated pocket of finger-like in shape, as illustrated in FIG. 2. The tripod support 27 is brought into position over the diverticulum 51 by observation through the fibers 15. Some of the fibers carry light to the diverticula, while other fibers return the visual light reflection from the diverticula. It may be necessary to inject water and/or air through opening 22 to clean the site of the diverticula 51. Once the tripod support 27 is properly in place, as illustrated in FIG. 3, the vacuum tube 32 is maneuvered forwardly such that the end 33 confronts the opening 52 in the diverticula 51. The tube 32 may be further extended such that the end 33 moves into the diverticula 51 until it confronts the bottom end 53 of diverticula 51 as illustrated in FIG. 4. A vacuum is then applied through tube 32 and the tube 32 is withdrawn as shown in FIG. 5, pulling the diverticula 51 into the tube 36, completely inverting the diverticula 51. Simultaneously the tube 36 may be extended forwardly until it approaches the ring 28 of tripod support 27 as illustrated in FIG. 5. The caliper 39 is then moved forwardly until the portions 42 and 43 lie between the first and second rubber bands on tube 36. The portion 42, 43 are then rotated toward one another, thus grasping the rubber band 38 to be removed and applied to the diverticula 51 as illustrated in FIG. 6. The rubber band 38 then contracts closing the inverted diverticula 51. The tube 36 may then be withdrawn, the vacuum of tube 32 released and the elongated tube 12 moved to another site for treatment in a similar manner of another diverticula.

While a particular embodiment of the present invention is illustrated in FIGS. 1-7, various modifications may be made without departing from the broader scope of the present invention. For example, the tube 36 may alternately carry a plurality of staples which may be suitably removed by the caliper 39 and collapsed around an inverted diverticula in a manner much like that illustrated with the rubber band. Alternatively, a slip noose may be carried on the tube 36 with an end attached to the caliper 39. When the noose is inserted over the inverted diverticulum, and the caliper is withdrawn, the caliper may draw on the free end of the noose to tighten the noose down around the inverted diverticula in a manner similar to the rubber band 38.

What is claimed is:

1. The method of treating tissue protrusions extending outward from the colon or from the intestine comprising the steps of:
   inserting a tube in a first direction into a tissue protrusion extending outward from the colon or the intestine;
   applying a vacuum with an end of the tube only to an inner end of the tissue protrusion to hold the inner end of the tissue protrusion relative to the end of the tube; and
   moving the tube in a direction opposite to the first direction while applying the vacuum to the inner end of the tissue protrusion to invert the tissue protrusion.

2. The method of claim 1, further comprising the step of fastening the tissue protrusion in the inverted condition to maintain the tissue protrusion in the inverted condition.

3. The method of claim 2, wherein the step of fastening includes the steps of:
stretching a rubber band;
positioning the rubber band in the stretched state adjacent the tissue protrusion in the inverted condition; and
releasing the rubber band from the stretched state so that the rubber band engages the tissue protrusion in the inverted condition.

4. The method of claim 3, wherein the step of fastening includes the steps of:
providing an outer tube surrounding the tube for applying the vacuum;
positioning the rubber band in the stretched state on the outer tube;
positioning an end of the outer tube adjacent a desired location relative to the tissue protrusion; and
sliding the rubber band past the end of the outer tube to release the rubber band from the stretched state and into engagement with the tissue protrusion.

5. The method of claim 4, further comprising the step of providing an endoscopic apparatus, the tube for applying the vacuum and the outer tube each being separately movable relative to the endoscopic apparatus.

6. The method of claim 1, before the step of moving the tube in the direction opposite to the first direction, further comprising the step of engaging tissue in an area surrounding the tissue protrusion with a support member to provide support when the tissue protrusion is inverted, the tube being movable relative to the support member.

7. A method of treating tissue protrusions extending into the colon or into the intestine comprising the steps of:
providing an inner tube and an outer tube, the outer tube surrounding at least a portion of the inner tube, the outer tube being movable relative to the inner tube;
placing at least one rubber band in a stretched state about the outer tube;
applying a vacuum with the inner tube only to an end of the tissue protrusion to hold the tissue protrusion for treatment;
moving the outer tube to position the rubber band in the stretched state adjacent a desired location relative to the tissue protrusion; and
removing the rubber band from the outer tube so that the rubber band is no longer in the stretched state and the rubber band engages the tissue protrusion.

8. The method of claim 7, further comprising the step of engaging tissue in an area surrounding the tissue protrusion with a support member to provide support when the tissue protrusion is held for treatment.

9. The method of claim 7, wherein the step of removing the rubber band from the outer tube comprises the step of sliding the rubber band past an end of the outer tube into engagement with the tissue protrusion.

10. The method of claim 7, further comprising the step of providing an endoscopic apparatus including a flexible tubular member extending between terminal front and rear parts, the endoscopic apparatus further including a guide mechanism for controlling movement of the front part relative to the rear part, the endoscopic apparatus further including an optical system to permit viewing at the back part of the surroundings and any activity adjacent the front part, the inner tube and the outer tube both extending from the front part and each being separately movable relative to the endoscopic apparatus.

* * * * *

UNITED STATES PATENT AND TRADEMARK OFFICE
CERTIFICATE OF CORRECTION

PATENT NO. : 5,224,497
DATED : July 6, 1993
INVENTOR(S) : Robert L. Ehlers

It is certified that error appears in the above-identified patent and that said Letters Patent is hereby corrected as shown below:

At Column 1, line 6, insert --now issued as U.S. Patent No. 5,100,419 on March 31, 1992,-- after the year "1990".

At Column 1, line 8, "Jul. 5" should read --July 6--.

At Column 1, line 19, "diverticular" should read --diverticula--.

At Column 1, line 22, "reside" should read --residue--.

At Column 1, line 67, delete "a" after the word --is--.

At Column 1, line 68, insert --a-- after the word "having".

At Column 2, line 5, "diverticular" should read --diverticula--.

At Column 2, line 7, delete "Cl" after the word "wall".

At Column 2, line 44, "onto" should read --into--.

At Column 2, line 58, 59 "provided" should read --provide--.

At Column 2, line 65, insert --the-- after the word "of".

UNITED STATES PATENT AND TRADEMARK OFFICE
CERTIFICATE OF CORRECTION

PATENT NO. : 5,224,497

DATED : July 6, 1993

INVENTOR(S) : Robert L. Ehlers

It is certified that error appears in the above-identified patent and that said Letters Patent is hereby corrected as shown below:

At Column 4, line 10, "5" should read --51--.

Signed and Sealed this

Twenty-first Day of June, 1994

Attest:

BRUCE LEHMAN

*Attesting Officer*     *Commissioner of Patents and Trademarks*